United States Patent [19]
Brennen

[11] Patent Number: 5,741,321
[45] Date of Patent: Apr. 21, 1998

[54] ACTIVE FIXATION MEDICAL ELECTRICAL LEAD HAVING IMPROVED TURNING TOOL

[75] Inventor: Kenneth R. Brennen, Fridley, Minn.

[73] Assignee: Medtronic, Inc., Minneapolis, Minn.

[21] Appl. No.: 585,218

[22] Filed: Jan. 11, 1996

[51] Int. Cl.⁶ .................................................. A61N 1/05
[52] U.S. Cl. .................................................... 607/127
[58] Field of Search .................................. 607/126, 127, 607/128, 131; 128/642

[56] References Cited

U.S. PATENT DOCUMENTS

| | | |
|---|---|---|
| 4,624,266 | 11/1986 | Kane . |
| 4,967,766 | 11/1990 | Bradshaw . |
| 5,020,545 | 6/1991 | Soukup . |
| 5,056,516 | 10/1991 | Spehr . |
| 5,228,455 | 7/1993 | Barcel . |

*Primary Examiner*—Scott Getzow
*Attorney, Agent, or Firm*—Michael J. Jaro; Harold Patton

[57] ABSTRACT

An active-fixation medical electrical lead having an improved turning tool. In particular, the lead has a fixation helix attached to a coiled conductor, the coiled conductor is attached at the opposite end to a connector assembly. The coiled conductor is covered by an insulative sheath between the fixation helix and the connector assembly. Mating with the connector assembly is the improved turning tool. The turning tool features essentially three components: housing, roller assembly and header. Housing is shaped so as to frictionally couple with a sealing ring of the connector assembly while permitting a connector pin to of the connector assembly to extend therethrough and into roller assembly. Through such a combination the roller assembly may be rotated relative to housing thereby causing connector pin to rotate relative to sealing ring and thus extend or retract a fixation helix. Header further permits a stylet to be guided through turning tool and remain within lead while in use. Ultimately such a device permits a physician to extend as well as retract a helix with only one hand.

6 Claims, 4 Drawing Sheets

ACTIVE FIXATION MEDICAL ELECTRICAL LEAD HAVING IMPROVED TURNING TOOL

FIELD OF THE INVENTION

This invention relates to the field of body-implantable medical device systems, and in particular to a body-implantable medical device system which includes an active fixation medical electrical lead having an improved turning tool.

BACKGROUND OF THE INVENTION

In the medical field, various types of body-implantable leads are known and used. Cardiac pulse generators, in particular, use implanted leads to both sense cardiac function and deliver stimulation pulses. One type of commonly used implantable lead is an endocardial lead.

Endocardial leads are attached at their proximal end to an implantable pulse generator and at their distal end to the endocardium of a cardiac chamber. Often the lead assembly is inserted into the heart through a vein. The lead generally has an inner conductor covered by an insulative sheath.

The distal end of an endocardial lead may engage the endocardium by either an active fixation mechanism or a passive fixation mechanism. Passive fixation mechanisms, such as a tine assembly, lodge or passively fix the lead to the heart. Active fixation mechanisms use a structure, such as a helix or hook, to engage into or actively fix themselves to the heart.

A sharpened helix has been found to provide a reasonably secure means for fixing the lead to the heart. An exposed sharpened helix may damage a vein, however, during introduction. Thus many active fixation leads have helixes which either retract into the lead body or are shielded during introduction. See for example, U.S. Pat. No. 4,972,848 of Di Domenico (helix shielded within lead body which may be extended to engage cardiac tissue); U.S. Pat. No. 5,003,992 of Holleman et al. (plunger through helix guards against damage to tissue by the helix and may be retracted to engage cardiac tissue) and U.S. Pat. No. 4,827,940 of Mayer et al. (soluble cover shields helix until positioned proximate fixation site.) Among the most preferred methods of shielding a helix is where the helix may be retracted within or extended from the lead body.

On example of the more common means for extending or retracting a helix may be seen in the U.S. Pat. No. 4,106,512 of Bisping. As seen, such a lead design features a fixation helix to be retracted within or extended from the lead body which is actuated by rotation of the conductor. In particular, rotation of the connector pin rotates the conductor coil, which in turn rotates the fixation helix, thereby causing it to extend or retract.

Presently, so-called "Bisping" leads require a connector pin wrench to rotate the connector pin to thus extend or retract the fixation helix, as depicted in FIG. 1. As seen, connector pin wrench is attached to connector pin and is rotated by holding the connector assembly in one hand and rotating the wrench with the other hand.

SUMMARY OF THE INVENTION

Thus it is an object of the present invention to provide an active fixation lead having an improved turning tool which will permit a fixation helix to be retracted within or extended from the lead body with only one hand.

The above and other objects are met by the present invention which is directed to an active-fixation medical electrical lead having an improved turning tool. In particular, the lead has a fixation helix attached to a coiled conductor, the coiled conductor is attached at the opposite end to a connector assembly. The coiled conductor is covered by an insulative sheath between the fixation helix and the connector assembly. Mating with the connector assembly is the improved turning tool. The turning tool features essentially three components: housing, roller assembly and header. Housing is shaped so as to frictionally couple with a sealing ring of the connector assembly while permitting a connector pin to of the connector assembly to extend therethrough and into roller assembly. Through such a combination the roller assembly may be rotated relative to housing thereby causing connector pin to rotate relative to sealing ring and thus extend or retract a fixation helix. Header further permits a styler to be guided through turning tool and remain within lead while in use. Ultimately such a device permits a physician to extend as well as retract a helix with only one hand.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein.

The figures are not necessarily to scale.

DETAILED DESCRIPTION OF THE INVENTION

For the purposes of this specification and claims, the term "lead" is used herein in its broadest sense and includes a stimulation lead, a sensing lead, a combination thereof or any other elongated member, such as a catheter, which may usefully be introduced into a body.

Figure 1:
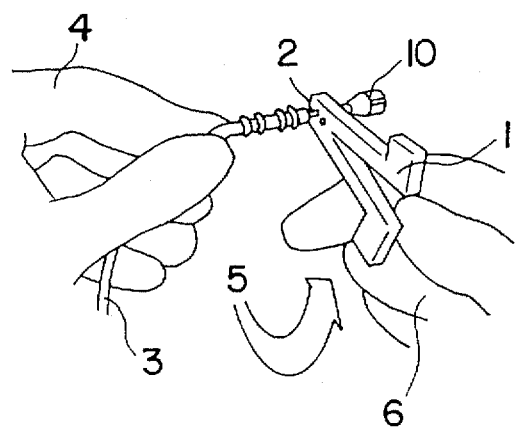
FIG. 1 is a perspective view of a prior art connector pin wrench attached to a connector pin.

As previously discussed, FIG. 1 depicts the operation of the connector pin wrench of the prior art. As seen, the connector pin wrench 1 was connected to the connector pin 2 of a lead 3. Lead 3 was held with one hand 4 while connector pin wrench 1 was rotated in direction 5 with the opposing hand 6. As such, the prior art connector pin wrench 1 required two hands to manipulate. As seen, styler 10 was permitted to be in place within lead. This is important as lead maneuverability is greatly enhanced by a stylet.

Figure 2:
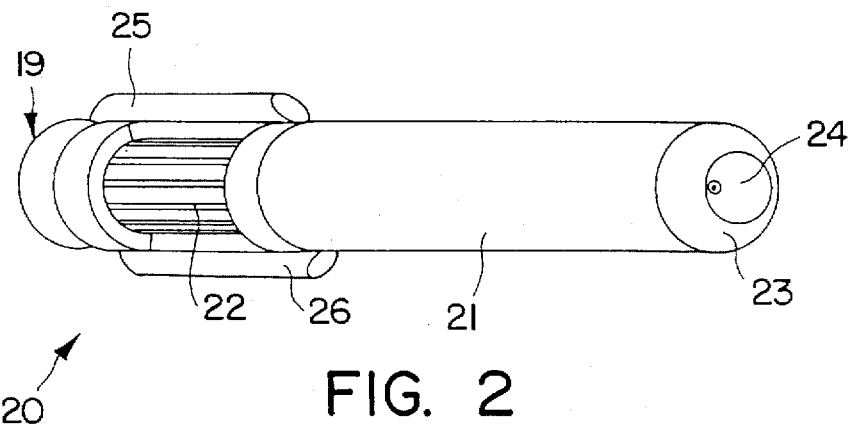
FIG. 2 is a perspective view of an improved turning tool according to the present invention.

FIG. 2 is a perspective view of an improved turning tool 20 for use in the present invention. As seen, turning tool has essentially three components: housing 21, roller assembly 22 and header 23. Proximal end of header 23 features a funnel shaped opening 24 designed to guide a stylet into guide tube (discussed below). Housing 21 features connector bars 25, 26 near distal end 19. Connector bars 25, 26 are rounded and spaced far enough away from the surface of the roller assembly 22 to avoid pinching a rubber glove during manipulation.

Figure 3:
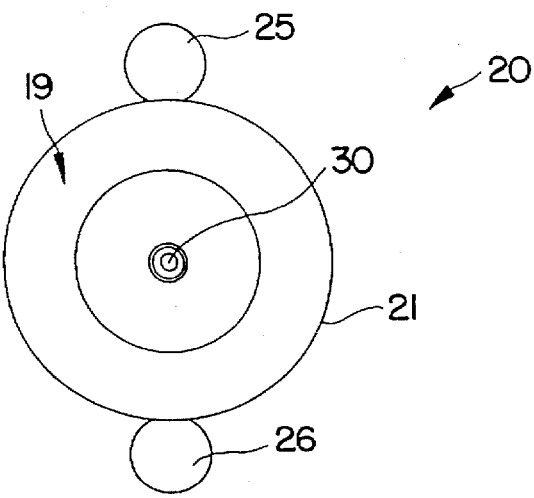
FIG. 3 is a view of the distal end of the turning tool shown in FIG. 2.

Turning to FIG. 3, which shows the distal end 19 of housing 21. As seen the distal end of housing 21 features a connector pin hole 30 which is sized to have connector pin inserted therethrough. Connector pin when inserted through connector pin hole meets with roller assembly 22, depicted in detail in FIG. 4.

Figure 4:
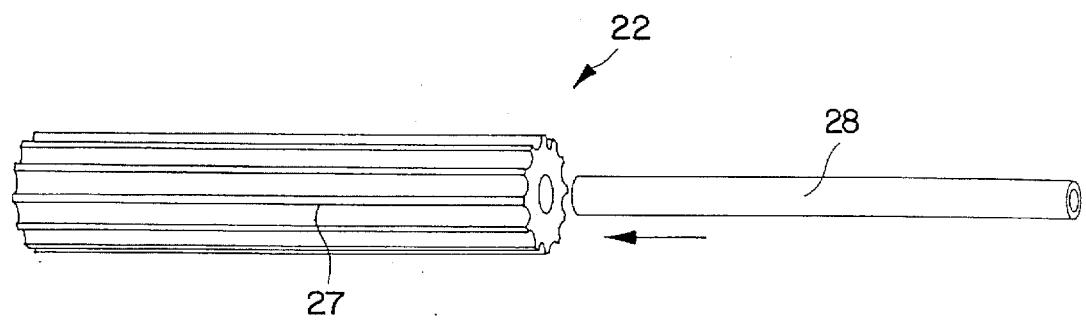
FIG. 4 is an exploded view of the roller assembly used in the improved turning tool.

As seen in FIG. 4, roller assembly 22 has two parts, a roller 27 and an elastomeric friction tube 28. Friction tube 28 is sized to be inserted through and fit within the lumen through roller 27. The diameter of lumen within friction tube 28 is sized, in turn, to form a friction fit over a connector pin. In the preferred embodiment, the diameter of lumen within friction tube 28 is approximately 0.056 inches in diameter which corresponds to a standard size connector pin, such as the industry standard IS1 or IS2. Roller assembly 22 has a knurled surface and is sized to mate with plastic header 23, as depicted in FIG. 5.

Figure 5:
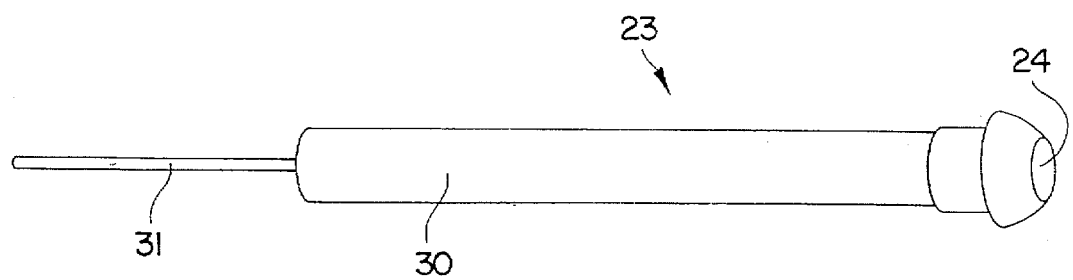
FIG. 5 is a perspective view of the header used in the improved turning tool.

FIG. 5 depicts header 23. As seen, header 23 has two parts, header body 30 and guide tube 31 therethrough. Header body 30 features at proximal end a funnel shaped opening 24 to guide stylet (not shown) into the guide tube 31. Guide tube 31 is mounted within header body 30.

Figure 6:
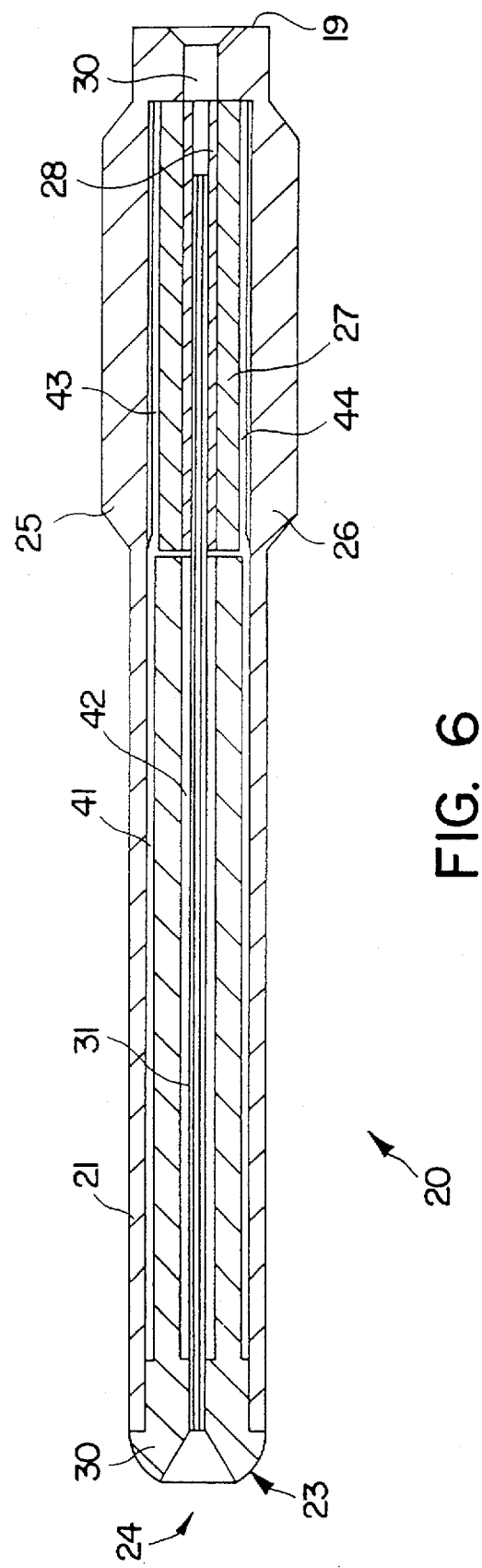
FIG. 6 is a cross sectional view of the improved turning tool shown in FIG. 1.
Figure 7:
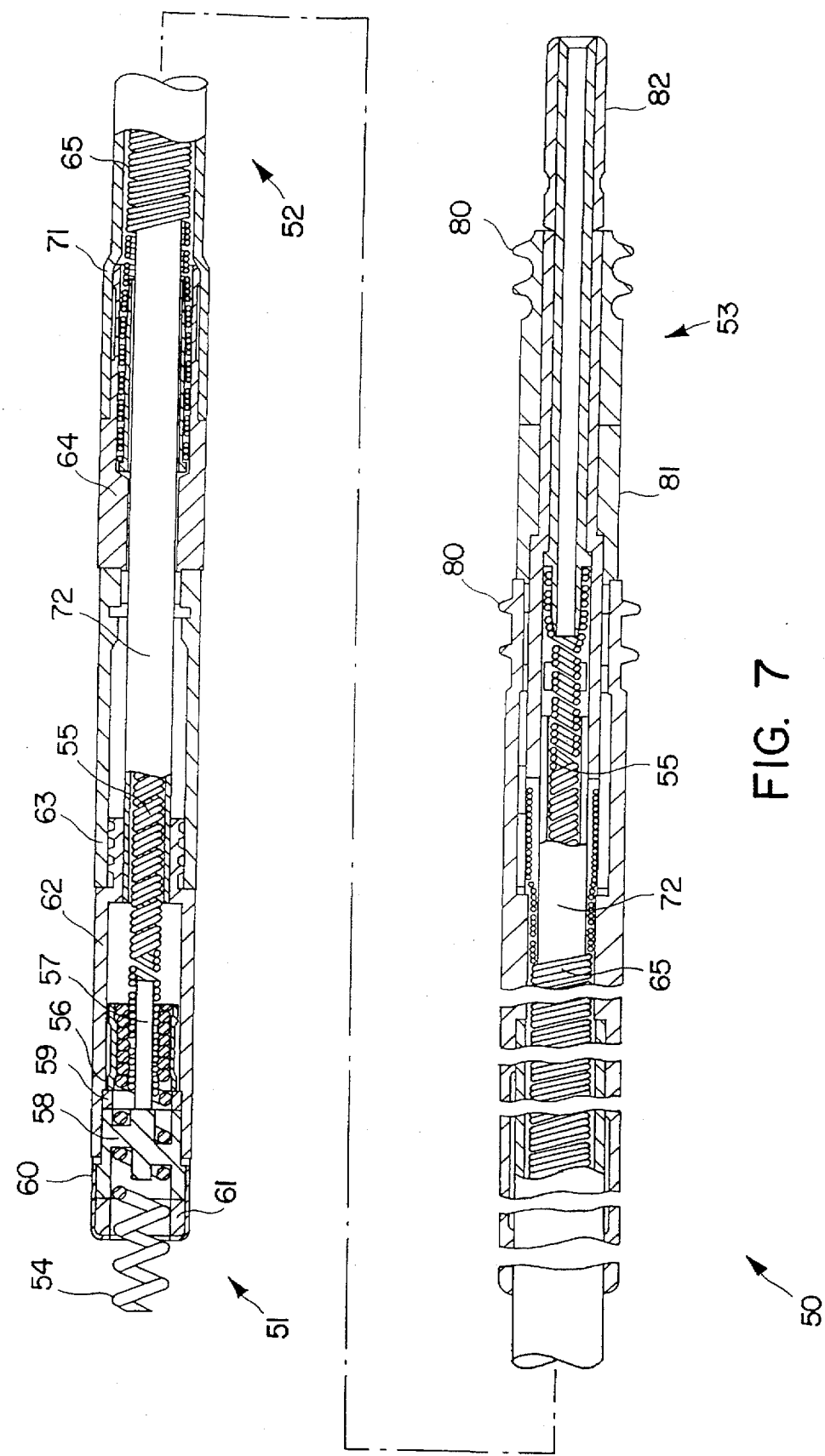
FIG. 7 is a greatly enlarged side cross-sectional view of a medical electrical lead having active fixation which may be extended or retracted with the improved turning tool shown in FIG. 2.

FIG. 6 is a cross sectional view of the turning tool 20. As seen, proximal end of header 23 has a funnel shaped opening 24 designed to guide a stylet into guide tube. As further seen header body 30 is designed so as to have a spacing 41 (shown here as an almost solid line) between itself and housing 21, as well as to have a further spacing 42 between itself and guide tube 31. This provides for spacings suitable for aeration during the sterilization process, preferably using ethylene oxide as is well known in the art. As seen guide tube 31 extends into the lumen of roller 27, and in particular within friction tube 28. As also seen connector bars 25, 26 are separated from the surface of the roller assembly 22 by spacings 43 and 44 to avoid pinching a rubber glove during manipulation.

Turning tool is constructed of the following materials: Header body 30, housing 21 and roller 27 are made from polysulfone, although any other resterilizable polymer or material may also be used. Guide tube 31 is made of stainless steel while friction tube 28 is made from silicone, although other elastomeric materials may also be used.

Turning now to FIG. 6 which depicts a medical electrical lead having an active fixation which may be activated using the improved turning tool. As seen, lead 50 has essentially 3 sections: electrode assembly 51, lead body 52 and connector assembly 53. Electrode assembly 51 features a helix 54 fitted about inner conductor 55 using crimp 56 and core pin 57. Helix 54 is disposed through a cap seal assembly 58 and indicator ring 59. At distal end is MCRD cap 60 around which is fitted an MCRD 61. MCRD 61 is provided to elute asteroid or any other anti-inflammatory drug in the area about helix 54. Proximal to MCRD cap 60 is sleeve head 62. Sleeve head 62 meets into TR spacer 63 which in turns leads to electrode ring 64. Electrode ring 64 meets with outer coiled conductor 65. Covering outer coiled conductor 65 is outer insulated sleeve 71 while inner coil conductor 55 is covered by inner insulated sleeve 72.

In the preferred embodiment, inner and outer insulative sleeves 71, 72 are constructed from polyurethane, although other biocompatible insulators may be used, such as silicone.

Conductors 55, 65 are preferably MP35N although other biocompatible conductors maybe used. Conductors are furthermore multifilar as is well known in the arts.

Helix 54 and electrode ring 64 are preferably a polished platinum alloy although other biocompatible conductors maybe used.

Lead body 52 thus, is essentially inner coiled conductor 55 covered by inner insulated sheath 72 which in turn is covered by outer coiled conductor 65 and finally covered by outer insulative sheath 71.

At proximal end of lead body 52 is connector assembly 53. As seen, connector assembly 53 essentially has sealing rings 80 disposed on either side of connector ring 81. At most proximal end of connector assembly 53 is connector pin 82. Connector ring 81 is electrically coupled to outer conductor 65 while connector pin 82 is electrically coupled to inner conductor 55. Through such a construction, connector pin 82 is thus electrically coupled to ring electrode 64 while connector pin 82 is electrically coupled to helix 54. Connector pin 82, moreover, is mechanically coupled as seen to inner conductor 55 such that rotation of connector pin 82 in a first direction causes helix 54 to rotate in the first direction.

As is well known in the art, the improved turning tool is used to implant the lead and manipulate the helix. In particular the tool is mated with the connector pin during the lead implantation process in order to provide a means for extending or retracting the fixation helix. Once the helix is properly positioned the tool is removed from the connector pin and the lead is electrically coupled to a pulse generator. The turning tool is not implanted with the lead.

Although a specific embodiment of the invention has been disclosed, this is done for the purposes of illustration and is not intended to be limiting with regard to the scope of the invention. It is contemplated that various substitutions, alterations, and/or modifications, including but not limited to those specifically discussed herein, may be made to the disclosed embodiment of the invention without departing from the spirit and scope of the invention as defined in the appended claims, which follow.

What is claimed is:

1. A medical electrical lead system comprising:
   a medical electrical lead, the lead having a fixation helix coupled to a first end of a coiled conductor, a second end of the coiled conductor coupled to a connector pin, the coiled conductor covered between the first end and the second end by an insulative sheath, a sealing ring mounted to a proximal end of the insulative sheath; and
   a turning tool coupled to the connector pin, the turning tool having a housing, the housing having proximal end and a distal end, the distal end having a distal lumen, the distal lumen sized to frictionally engage the sealing ring, a roller assembly mounted with the housing and rotatable relative to the housing, the roller assembly having a inner lumen having an inner lumen diameter, the inner lumen diameter sized to frictionally engage the connector pin whereby rotation of the roller assembly relative to the housing causes the connector pin to rotate relative to the sealing ring.

2. A medical electrical lead system according to claim 1, wherein the roller assembly has a roller assembly lumen, a friction tube mounted within the roller assembly lumen.

3. A medical electrical lead system according to claim 1 wherein the distal lumen is funnel-shaped.

4. A medical electrical lead system according to claim 1 further comprising a header fitted with the lumen of the housing.

5. A turning tool for retracting and extending a helix of a medical electrical lead comprising
- a housing having a first end and a second end, the housing having a lumen between the two ends, the housing having an opening positioned between the first end and the second end, the second end having a sealing ring lumen therethrough, the sealing ring lumen sized to frictionally engage a sealing ring of a medical electrical lead;
- a header positioned in the first end, the header having proximal opening and a guide tube mounted to therewith, the header further having a distal end, the guide tube communicating with the distal opening of the header;
- a roller assembly mounted within the housing lumen, the roller assembly having a connector pin lumen therethrough.

6. A medical electrical lead system, the system having a medical electrical lead and a turning tool comprising:
- a medical electrical lead, the lead having a fixation helix coupled to a first end of a first coiled conductor, a second end of the first coiled conductor coupled to a connector pin, the lead further having a ring electrode, the ring electrode coupled to a first end of a second coiled conductor, a second end of the second coiled conductor coupled to a connector ring; the coiled second conductor covered between the first end and the second end by an first insulative sheath, a sealing ring mounted to a proximal end of the insulative sheath; and
- a turning tool coupled to the connector pin, the turning tool having a housing, the housing having a distal lumen, the distal lumen sized to frictionally engage the sealing ring, a roller assembly mounted within the housing and rotatable relative to the housing, the roller assembly having a inner lumen having an inner lumen diameter, the inner lumen diameter sized to frictionally engage the connector pin whereby rotation of the roller assembly relative to the housing causes the connector pin to rotate relative to the sealing ring.

* * * * *